(12) United States Patent
Ishii et al.

(10) Patent No.: US 7,019,179 B2
(45) Date of Patent: Mar. 28, 2006

(54) PROCESS FOR PRODUCING AROMATIC COMPOUNDS

(75) Inventors: Yasutaka Ishii, Takatsuki (JP); Tatsuya Nakano, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 226 days.

(21) Appl. No.: 10/379,603

(22) Filed: Mar. 6, 2003

(65) Prior Publication Data

US 2003/0171625 A1  Sep. 11, 2003

(30) Foreign Application Priority Data

Mar. 7, 2002 (JP) ............................ 2002-062663
Mar. 7, 2002 (JP) ............................ 2002-062664
Mar. 8, 2002 (JP) ............................ 2002-063034

(51) Int. Cl.
  *C07C 39/04* (2006.01)
  *C07C 39/06* (2006.01)
  *C07C 39/07* (2006.01)
  *C07C 39/08* (2006.01)
  *C07C 39/11* (2006.01)

(52) U.S. Cl. ............... 568/716; 568/715; 568/717; 568/718; 568/712; 568/720; 568/723; 568/731

(58) Field of Classification Search ............... 562/406; 568/715, 716, 717, 718, 719, 720, 723, 731
See application file for complete search history.

(56) References Cited

U.S. PATENT DOCUMENTS 3,763,213 A  10/1973  Heck
3,783,140 A  1/1974  Heck

FOREIGN PATENT DOCUMENTS

| DE | 501467 C | 7/1930 |
| DE | 584762 C | 9/1933 |
| DE | 586878 C | 10/1933 |
| GB | 2066815 A | 7/1981 |
| JP | 06116187 A * | 4/1994 |

OTHER PUBLICATIONS

Louis et al., Indian Journal of Chemistry, vol. 40A, pp. 837-840, (Aug. 2001).
Wada et al., Chemistry Letters, pp. 1209-1210, (1997).

* cited by examiner

*Primary Examiner*—Elvis O. Price
(74) *Attorney, Agent, or Firm*—Birch, Stewart, Kolasch & Birch, LLP

(57) ABSTRACT

A process produces an aromatic compound by bringing an aromatic compound (B) into contact with molecular oxygen (C) in the presence of a catalyst (A) comprising at least one of (A1) a heteropolyacid and/or a salt thereof, and (A2) a mixture of oxoacids and/or salts thereof containing, as a whole, one of P and Si and at least one selected from V, Mo and W to thereby yield another aromatic compound (G) than the aromatic compound (B). The process can produce, for example, a corresponding aromatic hydroxy compound (G1) by allowing the aromatic compound (B) to react with the molecular oxygen (C) further in the presence of a reducing agent (D).

5 Claims, No Drawings

PROCESS FOR PRODUCING AROMATIC COMPOUNDS

BACKGROUND OF THE INVENTION

1. Field of the Invention

The present invention relates to a process for producing aromatic compounds, and specifically, it relates to a process for producing another aromatic compound from an aromatic compound by oxidation using molecular oxygen. More specifically, it relates to a process of subjecting an aromatic compound to direct oxidation using molecular oxygen to thereby produce a corresponding aromatic hydroxy compound; a process of subjecting an aromatic compound to oxidative coupling to thereby produce a corresponding aromatic compound including plural moieties of the aromatic compound directly combined with each other through a single bond; and a process of subjecting an aromatic compound to oxidative coupling with an olefin or an acetylene to thereby produce a corresponding aromatic compound having an alkenyl group or an alkynyl group. Such aromatic hydroxy compounds are useful as, for example, organic chemical materials, pharmaceutical materials, agrochemical materials, and polymer materials. The aromatic compounds each including plural moieties of an aromatic compound directly combined with each other through a single bond are useful as heat transfer media, raw materials in organic syntheses, dyes, and pharmaceutical materials. The aromatic compounds each having an alkenyl group or alkynyl group, such as stilbene, derivatives thereof, cinnamic acid, and derivatives thereof, are useful as polymer materials, dyes, synthetic intermediates for pharmaceuticals and other fine chemicals, and intermediate materials for other organic chemical products.

2. Description of the Related Art

Phenol has been industrially produced by a process comprising the steps of oxidizing cumene to yield cumene hydroperoxide and decomposing cumene hydroperoxide in the presence of an inorganic acid. In contrast, a process has been proposed to produce phenol by direct oxidation of benzene. However, this process requires high temperature and high pressure conditions, and demands have been made on processes for producing phenols under milder conditions.

An oxidative coupling reaction of an aromatic compound such as benzene using oxygen as an oxidizing agent is an ideal preparation process of aromatic ring assembly compounds with less burden on the environment and with high atom efficiency. This process generally uses a palladium compound as a catalyst, but its catalytic efficiency is not always sufficiently high.

An attempt has been made to produce a corresponding aromatic compound having an alkenyl group by oxidative coupling between an aromatic hydrocarbon and an olefin in the presence of a catalyst. This reaction enables activation of a carbon-hydrogen bond of the aromatic hydrocarbon by action of the catalyst to thereby form a novel carbon-carbon bond and becomes a focus of attention as an ideal reaction with high atom efficiency. For example, Acc, Chem. Res., 34, 633(2001) reports an oxidative coupling reaction between an arene and an alkene by catalysis of a palladium compound using benzoquinone/t-butyl hydroperoxide as a reoxidant. However, this process must use peroxides having low handleability.

SUMMARY OF THE INVENTION

Accordingly, an object of the present invention is to provide a process for efficiently producing an aromatic compound from another aromatic compound by means of a simple and easy procedure under mild conditions.

Specifically, a concrete object of the present invention is to provide a process for producing an aromatic hydroxy compound directly from an aromatic compound under mild conditions.

Another concrete object of the present invention is to provide a process for efficiently producing a corresponding aromatic compound such as an aromatic ring assembly compound from an aromatic compound by oxidative coupling reaction.

Yet concrete object of the present invention is to provide a process for efficiently producing a corresponding aromatic compound having an alkenyl group or alkynyl group from an aromatic compound and an olefin or acetylene using an oxidizing agent and/or catalyst with good handleability.

After intensive investigations to achieve the above objects, the present inventors have found that, by allowing an aromatic compound to react with oxygen using a specific catalyst, another aromatic compound than the material aromatic compound can be efficiently produced. More specifically, they have found that when an aromatic compound is allowed to react with molecular oxygen in the presence of the specific catalyst and a reducing agent, a corresponding aromatic hydroxy compound can be produced under relatively mild conditions; that when a palladium compound is used in combination with the specific catalyst in an oxidative coupling reaction of an aromatic compound, reoxidation of Pd species is accelerated to thereby efficiently yield a corresponding aromatic compound having plural moieties of the aromatic compound directly combined with each other through a single bond; and that when a palladium compound is used in combination with the specific catalyst in an oxidative coupling reaction between an aromatic compound and an olefin or acetylene using molecular oxygen, a corresponding aromatic compound having an alkenyl group or alkynyl group can be efficiently produced under relatively mild conditions. The present invention has been accomplished based on these findings.

Specifically, the present invention provides a process for producing an aromatic compound, including the step of bringing an aromatic compound (B) into contact with molecular oxygen (C) in the presence of a catalyst (A) to thereby yield another aromatic compound (G) than the aromatic compound (B), which catalyst (A) includes at least one of (A1) a heteropolyacid and/or a salt thereof, and (A2) a mixture of oxoacids and/or salts thereof containing, as a whole, one of P and Si and at least one selected from the group consisting of V, Mo, and W, the process further including at least one of the following steps (i), (ii), and (iii):

(i) allowing the aromatic compound (B) to react with the molecular oxygen (C) further in the presence of a reducing agent (D) to thereby yield a corresponding aromatic hydroxy compound (G1);

(ii) bringing the aromatic compound (B) into contact with the molecular oxygen (C) further in the presence of a palladium compound catalyst (E) to thereby yield a corresponding aromatic compound (G2) including plural moieties of the aromatic compound (B) directly combined with each other through a single bond; and (iii) allowing the aromatic compound (B) to react with an olefin or acetylene (F) and the molecular oxygen (C) further in the presence of a palladium compound catalyst (E) to thereby yield a corresponding aromatic compound (G3) having an alkenyl group or alkynyl group combined with its aromatic ring.

The process can efficiently produce an aromatic compound from another aromatic compound by means of a simple and easy procedure under mild conditions.

When the material aromatic compound is allowed to react with molecular oxygen in the presence of the specific catalyst and a reducing agent, direct hydroxylation of its aromatic ring can smoothly proceed even under mild conditions to thereby produce a corresponding aromatic hydroxy compound in a good yield.

When a palladium compound is used in combination with the specific catalyst in an oxidative coupling reaction of the material aromatic compound, the coupling reaction can smoothly proceed even under mild conditions to thereby efficiently produce a corresponding aromatic compound such as an aromatic ring assembly compound.

In addition, when a palladium compound is used in combination with the specific compound as catalysts in an oxidative coupling reaction of the material aromatic compound with an olefin or acetylene using molecular oxygen, a corresponding aromatic compound having an alkenyl group or alkynyl group can be efficiently produced even under mild conditions.

The heteropolyacid and/or a salt thereof (A1) may include, as its constitutional elements, one of P and Si and at least one selected from the group consisting of V, Mo, and W. The heteropolyacid and/or a salt thereof (A1) may be at least one of phosphovanadomolybdic acids, phosphomolybdic acids, and salts thereof represented by the following formula:

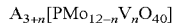

$$A_{3+n}[PMo_{12-n}V_nO_{40}]$$

wherein A is at least one selected from the group consisting of hydrogen atom, $NH_4$, alkali metals, and alkaline earth metals; and n is an integer from 0 to 10. The catalyst (A) preferably includes one of P and Si, 10.5 to 11.9 gram atom of Mo, and 0.1 to 1.5 gram atom of V relative to 1 gram atom of the one of P and Si.

The term "palladium compound" as used herein also includes elementary palladium as well as palladium compounds.

Further objects, features and advantages of the present invention will become apparent from the following description of the preferred embodiments.

DESCRIPTION OF THE PREFERRED EMBODIMENTS

Catalysts

The process of the present invention uses, as a catalyst, a catalyst (A) including at least one of (A1) a heteropolyacid and/or a salt thereof, and (A2) a mixture of oxoacids and/or salts thereof containing, as a whole, one of P and Si and at least one selected from the group consisting of V, Mo and W.

Such heteropolyacids are condensates of oxoacids each containing two or more different types of central ions and are called as heteronuclear poly acids (heteronuclear condensed acids). The heteropolyacids each comprise, for example, an oxoacid ion of P, As, Sn, Si, Ti, or Zr, such as phosphoric acid or silicic acid, and another oxoacid ion of V, Mo, or W, such as vanadic acid, molybdic acid, or tungstic acid. Combinations of these oxoacid ions can yield various heteropolyacids.

Heteroatoms of oxoacids constituting the heteropolyacids are not specifically limited and include, for example, Cu, Be, B, Al, C, Si, Ge, Sn, Ti, Zr, Ce, Th, N, P, As, Sb, V, Nb, Ta, Cr, Mo, W, U, Se, Te, Mn, I, Fe, Co, Ni, Rh, Os, Ir, and Pt. The heteropolyacids preferably each comprise at least one element selected from P, Si, V, Mo, and W. More preferably, they each comprise P and/or Si and at least one element selected from V, Mo and W. and further preferably comprise P and/or Si and at least one of V and Mo.

Heteropoly-anions constituting the heteropolyacids and salts thereof may have various compositions. The heteropoly-anions preferably have a composition represented by: $XM_{12}O_{40}$, wherein X is an element such as Si and P; and M is another element such as Mo, W, and V. Examples of heteropoly-anions having the composition are anions of phosphomolybdic acids, phosphotungstic acids, silicomolybdic acids, silicotungstic acids, and phosphovanadomolybdic acids.

The heteropolyacid may be a free heteropolyacid or a salt of a heteropolyacid, except with another cation replacing at least a part of hydrogen atoms corresponding to the cation of the heteropolyacid. Such cations capable of replacing the hydrogen atoms include, but are not limited to, cations of ammonium such as $NH_4$; alkali metals such as Cs, Rb, K, Na, and Li; and alkaline earth metals such as Ba, Sr, Ca, and Mg.

Among these heteropolyacids and salts thereof, preferred are phosphovanadomolybdic acids, phosphomolybdic acids, and salts thereof represented by the following formula:

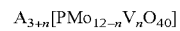

$$A_{3+n}[PMo_{12-n}V_nO_{40}]$$

wherein A is a heteropolyacid cation; and n is an integer from 0 to 10 and preferably from 1 to 10. Examples of the cation represented by A include hydrogen atom and the aforementioned cations. Among these heteropolyacids and salts thereof, typically preferred are phosphovanadomolybdic acids and phosphomolybdic acids of perfect proton type. Ammonium phosphovanadomolybdates and ammonium phosphomolybdates produced by replacing all of or a part of protons of a phosphovanadomolybdic acid and a phosphomolybdic acid respectively with $NH_4$ are also preferred in the production (iii) of the aromatic compound (G3) having an alkenyl group or alkynyl group combined with its aromatic ring. In these cases, the number n is generally from 0 to 4 and preferably from 1 to 4. Examples of such phosphovanadomolybdic acids of perfect proton type are $H_4PMo_{11}VO_{40}$, $H_5PMo_{10}V_2O_{40}$, $H_6PMo_9V_3O_{40}$, and $H_7PMo_8V_4O_{40}$.

The heteropolyacids and salts thereof may be anhydrous or may contain crystal water. They can be used as supported catalysts supported by carriers such as active carbon. Each of these heteropolyacids and salts thereof can be used alone or in combination.

The mixtures (A2) of oxoacids and/or salts thereof for use in the present invention are not specifically limited as long as they are mixtures each containing, as a whole, one of P and Si, and at least one element selected from V, Mo, and W. The term "oxoacid" as used herein also includes heteropolyacids. In contrast, the term "oxoacid in the narrow sense" does not include such heteropolyacids.

Such heteropolyacids containing at least one of P, Si, V, Mo, and W include, but are not limited to, phosphomolybdic acid, phosphotungstic acid, phosphovanadic acid, phosphovanadomolybdic acid, silicomolybdic acid, silicotungstic acid, and silicovanadic acid. The oxoacids in the narrow sense containing at least one of P, Si, V, Mo, and W include, but are not limited to, phosphoric acid, silicic acid, vanadic acid, molybdic acid, and tungstic acid. Salts of these heteropolyacids and oxoacids in the narrow sense include, for example, ammonium salts, alkali metal salts, and alkaline earth metal salts.

The mixtures (A2) of oxoacids and/or salts thereof include, for example, (1) a mixture of two or more different heteropolyacids and/or salts thereof, such as a mixture of phosphomolybdic acid or a salt thereof with phosphovanadic acid or a salt thereof; (2) a mixture of a heteropolyacid and/or a salt thereof with an oxoacid in the narrow sense or a salt thereof, such as a mixture of phosphomolybdic acid or a salt thereof with vanadic acid or a salt thereof, and a mixture of a phosphovanadic acid or a salt thereof with molybdic acid or a salt thereof; and (3) a mixture of two or more different oxoacids in the narrow sense and/or salts thereof, such as a mixture of phosphoric acid or a salt thereof, molybdic acid or a salt thereof, and vanadic acid or a salt thereof.

These oxoacids and salts thereof may be anhydrous or may contain crystal water. Among these mixtures (A2) of oxoacids and/or salts thereof, mixtures of oxoacids are preferred.

In preferred embodiments of the present invention, the catalyst (A), i.e., the catalyst (A1) or (A2), comprises Mo, V, and one of P and Si and contains from 10.5 to 11.9 gram atom, preferably from 10.8 to 11.8 gram atom, and more preferably from 11.2 to 11.7 gram atom of Mo, and 0.1 to 1.5 gram atom, preferably 0.2 to 1.2 gram atom, and more preferably from 0.3 to 0.8 gram atom of V relative to 1 gram atom of the one of P and Si (particularly relative to 1 gram atom of P). This configuration is typically preferred (ii) in the production of the aromatic compound (G2) comprising plural moieties of the material aromatic compound directly combined with each other through a single bond and (iii) in the production of the aromatic compound (G3) having an alkenyl group or alkynyl group combined with its aromatic ring. This type of catalysts can improve the activity of, and can reduce the amount of, the palladium catalyst.

In the catalysts (A1), the proportions of individual elements can be controlled within the aforementioned ranges by mixing two or more types of heteropolyacids or salts thereof having different compositions. Such a catalyst having proportions of the individual elements within the above-specified ranges can be prepared by mixing two or more of the phosphovanadomolybdic acids and/or salts thereof (where n is from 1 to 10) represented by the formula: $A_{3+n}[PMo_{12-n}V_nO_{40}]$, or by mixing a phosphovanadomolybdic acid or a salt thereof (n is from 1 to 10) represented by the formula: $A_{3+n}[PMo_{12-n}V_nO_{40}]$ with a phosphomolybdic acid or a salt thereof represented by the formula:

$A_3PMo_{12}O_{40}$.

The amount of the catalyst (A) is not specifically limited. In the production (i) of the aromatic hydroxy compound (G1), the amount is, for example, from about 0.00001 to about 0.5 mole, preferably from about 0.0001 to about 0.1 mole, and more preferably from about 0.0003 to about 0.01 mole per mole of the material aromatic compound (B). In the production (ii) of the aromatic compound (G2), the amount is, for example, from about 0.00001 to about 0.5 mole, preferably from about 0.0001 to about 0.1 mole, and more preferably from about 0.0005 to about 0.05 mole per mole of the material aromatic compound (B). In the production (iii) of the aromatic compound (G3), the amount is, for example, from about 0.00001 to about 0.5 mole, preferably from about 0.0001 to about 0.1 mole, and more preferably from about 0.001 to about 0.05 mole per mole of the compound which is used in a less amount between the material aromatic compound (B) and the olefin or acetylene (F).

Palladium Compound Catalysts (E)

The catalyst (A) and a palladium compound catalyst (E) are used in combination in the production (ii) of the aromatic compound (G2) and in the production (iii) of the aromatic compound (G3).

Such palladium compound catalysts (E) include, but are not limited to, metal palladium, zerovalent palladium complexes, and other zerovalent palladium compounds; palladium(II) acetate, palladium(II) cyanide, and other organic acid salts of divalent palladium, dichiorobis(benzonitrile)palladium(II), and other organic complexes of divalent palladium, palladium(II) fluoride, palladium(II) chloride, palladium(II) bromide, palladium(II) iodide, and other halides of divalent palladium, palladium(II) nitrate, palladium(II) sulfate, and other oxoacid salts of divalent palladium, palladium(II) oxide, palladium(II) sulfide, palladium(II) selenide, palladium(II) hydroxide, tetraamminepalladium (II) chloride, other inorganic complexes of divalent palladium, and other divalent palladium compounds.

Among these palladium compounds, preferred are palladium(II) acetate, and other organic acid salts and organic complexes of divalent palladium, palladium(II) chloride, and other halides of divalent palladium, palladium(II) sulfate, other oxoacid salts of divalent palladium, and other divalent palladium compounds.

The palladium compounds can be used as supported catalysts supported on a carrier such as active carbon, silica, alumina, zeolite and the like. In this case, the palladium compounds and the heteropolyacids or salts thereof or the like (the catalyst (A)) are dispersed and supported on the same carrier. The palladium compounds can be used in the form where palladium atom is introduced in a natural mineral such as hydrotalcite, hydroxyapatite and the like as a constituting element. Each of these palladium compounds can be used alone or in combination.

The amount of the palladium compound in the production (ii) of the aromatic compound (G2) comprising plural moieties of the material aromatic compound directly combined with each other through a single bond is, for example, from about 0.000001 to about 0.1 mole, preferably from about 0.00001 to about 0.01 mole, and more preferably from about 0.00005 to about 0.005 mole per mole of the material aromatic compound (B). In the production (iii) of the aromatic compound (G3) having an alkenyl group or alkynyl group combined with its aromatic ring, the amount is, for example, from about 0.000001 to about 0.5 mole, preferably from about 0.0001 to about 0.2 mole, and more preferably from about 0.005 to about 0.1 mole per mole of the compound which is used in a less amount between the material aromatic compound (B) and the olefin or acetylene (F).

In the production (i) of the aromatic hydroxy compound (G1) according to the process of the present invention, a palladium compound such as palladium acetate may be added to a reaction system, which palladium compound has been often used in combination with a heteropolyacid in conventional technologies. However, the addition of such a palladium compound may rather reduce the yield of the aromatic hydroxy compound (G1).

Additional Catalytic Components and Other Components

In the process of the present invention, the yields of the target aromatic hydroxy compound (G1) and the aromatic coupling products (G2) and (G3) can be significantly increased by adding at least one of alkali metal compounds, alkaline earth metal compounds, and bases including organic bases and inorganic bases. Among them, basic alkali metal compounds and alkaline earth metal compounds are preferred. Each of these components can be used alone or in combination.

Such alkali metal compounds include, but are not limited to, lithium acetate, sodium acetate, potassium acetate, cesium acetate, other carboxylic acids salts of alkali metals, and other organic acid salts of alkali metals; sodium methoxide, sodium ethoxide, and other alkoxides of alkali metals; sodium carbonate, potassium carbonate, and other carbonates of alkali metals; sodium hydrogencarbonate, potassium hydrogencarbonate, and other hydrogencarbonates of alkali metals; sodium chloride, potassium chloride, sodium sulfate, potassium sulfate, sodium phosphate, potassium phosphate, and other mineral acid salts of alkali metals.

Examples of the alkaline earth metal compounds are magnesium acetate, calcium acetate, other carboxylic acid salts of alkaline earth metals, and other organic acid salts of alkaline earth metals; magnesium carbonate, calcium carbonate, and other carbonates of alkaline earth metals; magnesium chloride, calcium chloride, magnesium sulfate, calcium sulfate, magnesium phosphate, calcium phosphate, and other mineral acid salts of alkaline earth metals.

Among them, sodium acetate, other carboxylic acid salts, and other organic acid salts of alkali metals and alkaline earth metals are preferred.

The amount of this component is, for example, from about 0.00001 to about 1.0 mole, preferably from about 0.0001 to about 0.5 mole, and more preferably from about 0.001 to about 0.1 mole per mole of the material aromatic compound (B) or per mole of the compound used in a less amount between the material aromatic compound (B) and the olefin or acetylene (F), if any.

When the palladium compound is used as a catalyst, its activity can be increased and the reaction yield can be significantly improved by adding a compound having coordinative ability to palladium (coordinative compound) to the system. Such coordinative compounds include, but are not limited to, acetylacetone, benzylideneacetone (benzalacetone), dibenzylideneacetone, and other carbonyl compounds; triphenylphosphine, methyldiphenylphosphine, dimethylphenylphosphine, and other phosphine compounds; cyclooctadiene, cyclopentadiene, and other non-aromatic unsaturated compounds; and aromatic compounds.

The amount of the coordinative compound is, for example, from about 0.00001 to about 1.0 mole, preferably from about 0.0001 to about 0.5 mole, and more preferably from about 0.001 to about 0.1 mole per mole of the material aromatic compound (B) or per mole of the compound used in a less amount between the material aromatic compound (B) and the olefin or acetylene (F), if any.

Reducing Agents (D)

In the production (i) of the aromatic hydroxy compound (G1) according to the process of the present invention, the reaction system must comprise a reducing agent (reducing substance) (D). Such reducing agents (D) are not specifically limited, as long as they are substances having reducing activity to other substances, and include, for example, carbon monoxide, hydrogen, silanes such as $SiH_4$, as well as aldehydes, alcohols, and other organic substances. When a reducing gas is used as the reducing agent (D), the reaction can be performed in an atmosphere of the reducing gas.

The amount of the reducing agent (D) is, for example, from about 0.001 to about 10 moles per mole of the material aromatic compound (B) and can be large excess to the aromatic compound (B) for further improving the conversion and/or yield.

Molecular Oxygen (C)

The molecular oxygen (C) is not specifically limited and includes, for example, pure oxygen, air, and diluted oxygen with an inert gas such as nitrogen gas, helium gas, and argon gas.

The amount of the molecular oxygen (C) is generally equal to or more than about 0.5 mole, for example equal to or more than about 1 mole, preferably from about 1 to about 100 moles, and more preferably from about 1 to about 50 moles per mole of the material aromatic compound (B) or per mole of the compound used in a less amount between the material aromatic compound (B) and the olefin or acetylene (F), if any. The molecular oxygen (C) can be used in large excess to the aromatic compound (B).

Aromatic Compounds (B)

In the production (i) of the aromatic hydroxy compound (G1) according to the process of the present invention, the material aromatic compounds (B) are not specifically limited, as long as they are compounds each having an aromatic ring having at least one moiety (e.g., a carbon-hydrogen bond) to which a hydroxyl group can be introduced. In the production (ii) of the aromatic compound (G2) comprising plural moieties of the material aromatic compound directly combined with each other through a single bond or in the production (iii) of the aromatic compound (G3) having an alkenyl group or alkynyl group combined with its aromatic ring, the aromatic compounds (B) are not specifically limited as long as they are compounds each having an aromatic ring having at least one moiety (e.g., a carbon-hydrogen bond) at which an oxidative coupling reaction can occur. The aromatic ring can be any of aromatic hydrocarbon rings and aromatic heterocyclic rings and may have at least one substituent within a range not adversely affecting the reaction.

The aromatic compounds (B) are represented by, for example, following Formula (1):

Ar-H (1)

wherein Ar is an aromatic cyclic group. In Formula (1), the aromatic cyclic group in Ar includes aromatic hydrocarbon groups and aromatic heterocyclic groups. Each of aromatic hydrocarbon rings in the aromatic hydrocarbon group and aromatic heterocyclic rings in the aromatic heterocyclic groups may have at least one substituent within a range not adversely affecting the reaction.

The aromatic hydrocarbon rings include, for example, benzene ring; condensed carbon rings such as naphthalene, azulene, indacene, anthracene, phenanthrene, triphenylene, pyrene, and other condensed carbon rings each comprising two to ten condensed 4- to 7-membered carbon rings.

The aromatic heterocyclic rings include, but are not limited to, heterocyclic rings each containing at least one oxygen atom as a heteroatom, such as furan, oxazole, isoxazole, and other 5-membered rings, 4-oxo-4H-pyran, and other 6-membered rings, benzofuran, isobenzofuran, 4-oxo-4H-chromene, and other condensed rings; heterocyclic rings each containing at least one sulfur atom as a heteroatom, such as thiophene, thiazole, isothiazole, thiadiazole, and other 5-membered rings, 4-oxo-4H-thiopyran, and other 6-membered rings, benzothiophene and other condensed rings; heterocyclic rings each containing at least one nitrogen atom as a heteroatom, such as pyrrole, pyrazole, imidazole, triazole, and other 5-membered rings, pyridine, pyridazine, pyrimidine, pyrazine, and other 6-membered rings, indole, quinoline, acridine, naphthyridine, quinazoline, purine, and other condensed rings.

Substituents which the aromatic rings (the aromatic hydrocarbon rings and aromatic heterocyclic rings) may have include, but are not limited to, alkyl groups such as methyl, ethyl, isopropyl, t-butyl, and other $C_1$–$C_4$ alkyl groups; alkenyl groups such as vinyl, allyl, and other $C_1$–$C_4$ alkenyl groups; alkynyl groups; alicyclic hydrocarbon groups; aromatic hydrocarbon groups such as phenyl, and naphthyl groups; acyl groups; heterocyclic groups; halogen atoms; hydroxyl group; mercapto group; substituted oxy groups such as methoxy group, other $C_1$–$C_4$ alkoxy groups, and other alkoxy groups, phenoxy group and other aryloxy groups, acetyloxy group and other acyloxy groups; substituted thio groups; carboxyl group; substituted oxycarbonyl groups such as methoxycarbonyl, ethoxycarbonyl, other $C_1$–$C_4$ alkoxy-carbonyl groups, and other alkoxycarbonyl groups; substituted or unsubstituted carbamoyl groups; cyano group; nitro group; substituted or unsubstituted amino groups such as amino group, N,N-dimethylamino group, and other N,N-di-$C_1$–$C_4$ alkylamino groups; sulfo group; and groups each comprising a plurality of these groups combined.

Examples of the aromatic compounds (B) include benzene, toluene, xylenes, mesitylene, ethylbenzene, styrene, phenylacetylene, biphenyl, acetophenone, benzophenone, chlorobenzene, bromobenzene, phenol, anisole, diphenyl ether, phenyl acetate, benzoic acid, phthalic anhydride, phthalimide, methyl benzoate, ethyl benzoate, benzamide, benzonitrile, nitrobenzene, aniline, N,N-dimethylaniline, other benzene and derivatives thereof; naphthalene, azulene, indacene, anthracene, phenanthrene, triphenylene, pyrene, and other aromatic hydrocarbons each comprising a plurality of condensed benzene rings, and derivatives thereof (e.g., naphthoquinone and anthraquinone); pyridine, furan, thiophene, and other aromatic heterocyclic compounds.

Each of the aromatic compounds (B) can be used alone or in combination in the production (ii) of the aromatic compound (G2) having plural moieties of the material aromatic compound directly combined with each other through a single bond.

Olefins and Acetylenes (F)

Material olefins and acetylenes (F) used in the production (iii) of the aromatic compound (G3) having an alkenyl group or alkynyl group combined with its aromatic ring are represented by following Formulae (2a) and (2b), respectively:

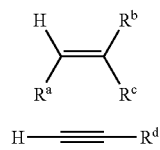

wherein $R^a$, $R^b$, $R^c$, and $R^d$ are the same or different and are each a hydrogen atom or an organic group, and wherein at least two of $R^a$, $R^b$, and $R^c$ maybe combined to form a ring with adjacent one or two carbon atoms.

Such organic groups are not specifically limited as long as they do not adversely affect the reaction and include, for example, hydrocarbon groups, heterocyclic groups, hydroxyl group, mercapto group, alkoxy groups, halogen atoms, N-substituted or unsubstituted amino groups, acyl groups and carbonyl-protected derivatives thereof, substituted oxycarbonyl groups, carboxyl group, substituted or unsubstituted carbamoyl groups, cyano group, substituted or unsubstituted iminoalkyl groups, nitro group, sulfur acid groups, and sulfur acid ester groups. The hydroxyl group, carboxyl group, and amino groups may be protected by a conventional protecting group.

The hydrocarbon groups include aliphatic hydrocarbon groups, alicyclic hydrocarbon groups, and aromatic hydrocarbon groups. Such aliphatic hydrocarbon groups include, but are not limited to, methyl, ethyl, propyl, isopropyl, butyl, isobutyl, s-butyl, t-butyl, pentyl, hexyl, octyl, decyl, tetradecyl, hexadecyl, octadecyl, vinyl, allyl, 1-propenyl, ethynyl, and other straight- or branched-chain aliphatic hydrocarbon groups (alkyl groups, alkenyl groups, and alkynyl groups) each containing from about 1 to about 20, preferably from about 1 to about 10, and more preferably from about 1 to about 6 carbon atoms.

The alicyclic hydrocarbon groups include, but are not limited to, cyclopropyl, cyclobutyl, cyclopentyl, cyclohexyl, cyclohexenyl, cyclooctyl, cyclodecyl, cyclododecyl, and other alicyclic hydrocarbon groups (e.g., cycloalkyl groups and cycloalkenyl groups) each containing from about 3 to about 20, and preferably from about 3 to about 15 carbon atoms.

The aromatic hydrocarbon groups include, for example, phenyl, naphthyl, and other aromatic hydrocarbon groups each containing from about 6 to about 20 carbon atoms.

These hydrocarbon groups may each have at least one substituent. Such substituent include, but are not limited to, halogen atoms such as fluorine, chlorine, bromine, and iodine atoms; oxo group; hydroxyl group which may be protected by a protecting group; hydroxymethyl group which may be protected by a protecting group; amino group which may be protected by a protecting group; carboxyl group which may be protected by a protecting group; substituted oxycarbonyl groups; substituted or unsubstituted carbamoyl groups; nitro group; acyl groups; cyano group; alkyl groups such as methyl, ethyl, and other $C_1$–$C_4$ alkyl groups; cycloalkyl groups; aryl groups such as phenyl, and naphthyl groups; and heterocyclic groups. Protecting groups conventionally used in the field of organic synthesis can be used as the protecting groups.

Heterocyclic rings constituting the heterocyclic groups in the organic groups include aromatic heterocyclic rings and non-aromatic heterocyclic rings. Such heterocyclic rings include, but are not limited to, heterocyclic rings each containing at least one oxygen atom as a heteroatom, such as furan, tetrahydrofuran, oxazole, isoxazole, and other 5-membered rings, 4-oxo-4H-pyran, tetrahydropyran, morpholine, and other 6-membered rings, benzofuran, isobenzofuran, 4-oxo-4H-chromene, chroman, isochroman, and other condensed rings; heterocyclic rings each containing at least one sulfur atom as a heteroatom, such as thiophene, thiazole, isothiazole, thiadiazole, and other 5-membered rings, 4-oxo-4H-thiopyran, and other 6-membered rings, benzothiophene and other condensed rings; heterocyclic rings each containing at least one nitrogen atom as a heteroatom, such as pyrrole, pyrrolidine, pyrazole, imidazole, triazole, and other 5-membered rings, pyridine, pyridazine, pyrimidine, pyrazine, piperidine, piperazine, and other 6-membered rings, indole, quinoline, quinoline, acridine, naphthyridine, quinazoline, purine, and other condensed rings. These heterocyclic groups may each have at least one substituent such as those exemplified in the description of the hydrocarbon groups.

The alkoxy groups in the organic groups include, for example, methoxy, ethoxy, propoxy, butoxy, and other alkoxy groups each containing from about 1 to about 6 carbon atoms. The halogen atoms include fluorine, chlorine, bromine, and iodine atoms. The N-substituted amino groups include, for example, N,N-dimethylamino, N,N-diethylamino, and piperidino groups. The acyl groups include, for example, formyl, acetyl, propionyl butyryl, (meth)acryloyl, cyclopentanecarbonyl, cyclohexanecarbonyl, benzoyl, naphthoyl, pyridylcarbonyl, and other aliphatic, alicyclic, aromatic, and heterocyclic acyl groups. The carbonyl-protected derivatives of the acyl groups include, for example, dimethylacetal, diethylacetal, 1,3-dioxane, 1,3-dioxolane, and other acetals; S,S'-dimethyldithioacetal, and other dithioacetals.

The substituted oxycarbonyl groups include, but are not limited to, methoxycarbonyl, ethoxycarbonyl, isopropoxycarbonyl, butoxycarbonyl, vinyloxycarbonyl, cyclopentyloxycarbonyl, cyclohexyloxycarbonyl, phenoxycarbonyl, benzyloxycarbonyl, pyridyloxycarbonyl, and acyloxycarbonyl groups (acid anhydride groups).

The substituted or unsubstituted carbamoyl groups include, but are not limited to, carbamoyl, N-methylcarbamoyl, N-phenylcarbamoyl, N,N-dimethylcarbamoyl, 1-pyrrolidinylcarbamoyl, and piperidinocarbamoyl groups. The sulfur acid groups include, for example, sulfo group (sulfonic acid group), and sulfinic acid group. The sulfur acid ester groups include, for example, methyl sulfonate, ethyl sulfonate, and other sulfonate groups; methyl sulfinate, ethyl sulfinate, and other sulfinate groups.

At least two of $R^a$, $R^b$, and $R^c$ may be combined to form a ring with one or two adjacent carbon atoms. Such rings include, but are not limited to, cyclopropane, cyclobutane, cyclopentane, cyclopentene, cyclohexane, cyclohexene, cyclooctane, cyclododecane, norbornene, and other alicyclic carbon rings (e.g., cycloalkane rings, cycloalkene rings, and bridged carbon rings) each having from about 3 to about 20 members. These rings may each have at least one substituent, and another ring (a non-aromatic ring or aromatic ring) may be combined to these rings.

Preferred substituents $R^a$, $R^b$, $R^c$, and $R^d$ include hydrogen atom; hydrocarbon groups such as $C_1$–$C_{10}$ aliphatic hydrocarbon groups, and other $C_1$–$C_{20}$ aliphatic hydrocarbon groups, phenyl, naphthyl, and other $C_6$–$C_{20}$ aryl groups, cycloalkyl groups having about 3 to about 8 members, and other cycloalkyl groups, trifluoromethyl group, other $C_1$–$C_4$ haloalkyl groups, other $C_1$–$C_6$ haloalkyl groups, and other haloalkyl groups; heterocyclic groups; substituted oxycarbonyl groups such as $C_1$–$C_6$ alkoxy-carbonyl groups, aryloxycarbonyl groups, aralkyloxycarbonyl groups, and cycloalkyloxycarbonyl groups; carboxyl group; substituted or unsubstituted carbamoyl groups; cyano group; nitro group; sulfur acid groups, sulfur acid ester groups, and acyl groups.

At least one of $R^a$, $R^b$, and $R^c$ is preferably an electron attracting group (electron withdrawing group). Such electron attracting groups include the aforementioned acyl groups and carbonyl-protected derivatives thereof, substituted oxycarbonyl groups, carboxyl group, substituted or unsubstituted carbamoyl groups, cyano group, substituted or unsubstituted iminoalkyl groups, nitro group, sulfur acid groups, and sulfur acid ester groups, as well as phenyl, naphthyl, and other aryl groups, 3-pyridyl, and other aromatic heterocyclic groups, vinyl, 1-propenyl, ethynyl, and other 1-alkenyl groups and 1-alkynyl groups, trifluoromethyl, and other haloalkyl groups.

The olefins represented by Formula (2a) may be any of α-olefins and internal olefins. The olefins also include dienes, and other olefins each having plural carbon-carbon double bonds. Typical examples of the olefins include ethylene, propylene, 1-butene, 2-butene, isobutene, 1-pentene, 2-pentene, 1-hexene, 2-hexene, 3-hexene, 1-heptene, 1-octene, 2-octene, 3-octene, 4-octene, 1-nonene, 1-decene, 1-dodecene, 1,5-hexadiene, 1,6-heptadiene, 1,7-octadiene, styrene, vinyltoluene, α-methylstyrene, 3-vinylpyridine, 3-vinylfuran, 3-vinylthiophene, (meth)acrylic acid, (meth)acrylic esters [e.g., methyl (meth)acrylate, ethyl (meth)acrylate, propyl (meth)acrylate, isopropyl (meth)acrylate, butyl (meth)acrylate, isobutyl (meth)acrylate, t-butyl (meth)acrylate, octyl (meth)acrylate, and 2-ethylhexyl (meth)acrylate], crotonic esters [e.g., methyl crotonate, and ethyl crotonate], 3-phenyl(meth)acrylic esters [e.g., methyl 3-phenyl (meth)acrylate, and ethyl 3-phenyl(meth)acrylate], maleic acid, fumaric acid, maleic esters (e.g., dimethyl maleate, diethyl maleate, and diisopropyl maleate), fumaric esters (e.g., dimethyl fumarate, diethyl fumarate, and diisopropyl fumarate), and other α,β-unsaturated carboxylic acids and derivatives thereof, (meth)acrylonitrile, acrolein, methacrolein, allyl alcohol, geraniol, α,β-unsaturated ketones [e.g., methyl vinyl ketone, divinyl ketone, benzylideneacetone, and dibenzylideneacetone], and other chain olefins (alkenes); cyclopentene, cyclohexene, cyclooctene, cyclodecene, cyclododecene, norbornene, dicyclopentadiene, cyclooctadiene, and other cyclic olefins (cycloalkenes, and bridged hydrocarbons each having at least one carbon-carbon double bond).

The acetylenes represented by Formula (2b) include, but are not limited to, acetylene, 1-propyne, 1-butyne, 1-pentyne, 1-hexyne, 1-heptyne, 1-octyne, phenylacetylene, and propiolic esters such as methyl propiolate, ethyl propiolate, isopropyl propiolate, propyl propiolate, and butyl propiolate.

Reactions

The reaction is performed in the presence of, or in the absence of, a solvent. The solvent can be appropriately selected according to the types of the material aromatic compound (B) and the olefin or acetylene (F), if any, and other conditions. Such solvents include, but are not limited to, water; acetic acid, propionic acid, trifluoroacetic acid, other carboxylic acids, and other organic acids; formamide, acetamide, dimethylformamide (DMF), dimethylacetamide, and other amides; nitromethane, nitroethane, and other nitro compounds; ethyl acetate, butyl acetate, and other esters; acetone, methyl ethyl ketone, and other ketones; diethyl ether, diisopropyl ether, dimethoxyethane, tetrahydrofuran, dioxane, and other chain or cyclic ethers; ethanol, propanol, butanol, t-butyl alcohol, and other alcohols; hexane, octane, and other aliphatic hydrocarbons; cyclopentane, cyclohexane, metylcyclohexane, and other alicyclic hydrocarbons; chloroform, dichloromethane, dichloroethane, carbon tetrachloride, and other halogenated hydrocarbons; and mixtures of these solvents.

Among these solvents, protic solvents are preferred. Specifically, water, organic acids, alcohols, and mixtures of these solvents are preferred in the production (i) of the aromatic hydroxy compound (G1). Carboxylic acids and other organic acids are preferred in the production (ii) of the aromatic compound (G2) comprising plural moieties of the material aromatic compound directly combined with each other through a single bond and in the production (iii) of the aromatic compound (G3) having an alkenyl group or alkynyl group combined with its aromatic ring.

In the production (iii) of the aromatic compound (G3), the molar ratio of the aromatic compound (B) such as the aromatic compound represented by Formula (1) to the olefin or acetylene (F) such as the compound represented by Formula (2a) or (2b) can be appropriately selected according to the types and combinations of the two compounds and is generally from about 0.8 to 50, preferably from about 1.5 to about 30, and more preferably from about 2 to about 20 for better reactivity. In this case, hydroquinone or another polymerization inhibitor may be added to the reaction system to prevent polymerization of the olefin or acetylene (F).

The process of the present invention enables the reaction to smoothly proceed even under relatively mild conditions. A reaction temperature can be appropriately selected according to the type(s) of the material compound(s) and other conditions and is, for example, from about 0° C. to about 250° C., generally from about 0° C. to about 200° C., preferably from about 40° C. to about 150° C., and more preferably from about 60° C. to about 120° C. The reaction can be performed at atmospheric pressure or under a pressure (under a load). The reaction is preferably performed under a pressure (under a load) in the production (i) of the aromatic hydroxy compound (G1). In this case, the reaction pressure is, for example, from about 0.1 to about 1 MPa, preferably from about 0.12 to about 2 MPa, and more preferably from about 0.15 to about 1 MPa in terms of oxygen partial pressure. In contrast, in the production (ii) of the aromatic compound (G2) and in the production (iii) of the aromatic compound (G3), the reaction pressure is, for example, from about 0.1 to about 5 MPa, and preferably from about 0.1 to about 2 MPa, and the reaction can sufficiently proceed even at atmospheric pressure (0.1 MPa). The reaction can be performed according to a conventional procedure such as batch system, semi-batch system, and continuous system in an atmosphere of, or under flow of, oxygen.

In the production (i) according to the process of the present invention, an oxidation reaction proceeds to thereby efficiently yield a corresponding aromatic hydroxy compound (such as a phenol) (G1) having a hydroxyl group introduced into an aromatic ring of the material aromatic compound (B).

In the production (ii), an oxidative coupling reaction proceeds to thereby yield a corresponding aromatic ring assembly compound (G2) having aromatic rings of the material aromatic compound (B) directly combined with each other through a single bond. When two or more different aromatic compounds (B) are used, an aromatic ring assembly compound having two or more different rings combined with each other through a single bond can be formed by cross coupling. An aromatic compound intramolecularly having plural aromatic rings, such as diphenyl ether, can yield a cyclic compound by action of an intramolecular coupling reaction. An aromatic compound having an alkyl group or another side chain on its aromatic ring may yield a coupling product having a single bond between the aromatic ring and the side chain (particularly at the benzyl position) in addition to, or instead of, the aromatic ring assembly compound. Under some reaction conditions, an aromatic hydroxy compound (a phenol) having a hydroxyl group directly combined with the aromatic ring of the material aromatic compound may be by-produced.

In the production (iii), an oxidative coupling reaction between the aromatic compound (B) and the olefin or acetylene (F) proceeds to thereby yield a corresponding aromatic compound (G3) having an alkenyl group (1-alkenyl group) or an alkynyl group (1-alkynyl group). For example, when the compound represented by Formula (1) is used as the aromatic compound (B) and the compound represented by Formula (2a) or (2b) is used as the olefin or acetylene (F), a compound represented by following Formula (3a) or (3b) is formed:

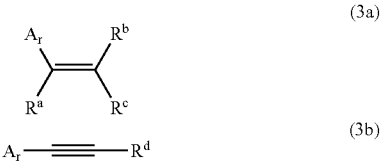

wherein Ar, $R^a$, $R^b$, $R^c$, and $R^d$ have the same meanings as defined above.

Under some reaction conditions, a compound comprising one molecule of the olefin or acetylene (F) oxidatively coupled with two or more molecules of the aromatic compound (B) and/or a compound comprising one molecule of the aromatic compound (B) oxidatively coupled with two or more molecules of the olefin or acetylene (F) can be formed. When propionic acid or another carboxylic acid containing 3 or more carbon atoms is used s the solvent, the reaction proceeds at a higher speed and often yields a compound comprising one molecule of the olefin or acetylene (F) oxidatively coupled with two or more molecules of the aromatic compound (B).

After the completion of the reaction, reaction products can be separated and purified by separation means such as filtration, concentration, distillation, extraction, crystallization, recrystallization, adsorption, and column chromatography, and combinations of these separation means.

EXAMPLES

The present invention will be illustrated in further detail with reference to several examples and comparative examples below, which are not intended to limit the scope of the invention.

Example 1

In an autoclave, 1.17 g (15 mmol) of benzene, 4.5 mg (0.02 mmol) of palladium(II) acetate, 33 mg (about 0.02 mmol) of $H_7PMo_8V_4O_{40}\cdot nH_2O$, 8 mg (0.1 mmol) of sodium acetate, and 5 ml of acetic acid aqueous solution (acetic acid:water=19:1) were placed and were stirred at a constant temperature of 90° C. in an atmosphere of air at 15 atm (1.5 MPa) and carbon monoxide gas at 5 atm (0.5 MPa) for 15 hours. The resulting reaction mixture was analyzed by gas chromatography to find that 1 mmol of phenol was produced in a yield of 6.7%.

Example 2

The procedure of Example 1 was repeated, except that palladium(II) acetate was not used. Consequently, 1.4 mmol of phenol was produced in a yield of 9.4%.

Example 3

The procedure of Example 1 was repeated, except that palladium(II) acetate was not used and that 35.6 mg (about 0.02 mmol) of $H_4PMo_{11}VO_{40}\cdot nH_2O$ was used instead of $H_7PMo_8V_4O_{40}\cdot nH_2O$. Consequently, 1.3 mmol of phenol was produced in a yield of 8.4%.

Example 4

The procedure of Example 2 was repeated, except that hydrogen gas (5 atm=0.5 MPa) was used instead of carbon monoxide gas. Consequently, 0.84 mmol of phenol was produced in a yield of 5.6%.

Example 5

The procedure of Example 2 was repeated, except that 15 mmol of mesitylene was used instead of benzene. Consequently, 0.53 mmol of 2,4,6-trimethylphenol was produced in a yield of 3.5%.

Example 6

The procedure of Example 2 was repeated, except that 15 mmol of benzoic acid was used instead of benzene. Consequently, 0.72 mmol of p-hydroxybenzoic acid was produced in a yield of 4.8%.

Example 7

The procedure of Example 2 was repeated, except that 15 mmol of methyl benzoate was used instead of benzene. Consequently, 0.81 mmol of methyl p-hydroxybenzoate was produced in a yield of 5.4%.

Comparative Example 1

The procedure of Example 1 was repeated, except that $H_7PMo_8V_4O_{40}$-$nH_2O$ was not used. Consequently, phenol was not produced, and the material was recovered.

Comparative Example 2

The procedure of Example 1 was repeated, except that carbon monoxide was not used. Consequently, only 0.3 mmol of phenol was produced.

Example 8

In a flask, 2.34 g (30 mmol) of benzene, 4.5 mg (0.02 mmol) of palladium(II) acetate, 323 mg (about 0.14 mmol) of $H_4PMo_{11}V_1O_{40}$-$nH_2O$, and 10 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that 1.52 g (9.8 mmol) of biphenyl, 0.29 g (1.3 mmol) of terphenyls, and 0.06 g (0.7 mmol) of phenol were produced.

Comparative Example 3

The procedure of Example 8 was repeated, except that $H_4PMo_{11}V_1O_{40}$-$nH_2O$ was not used. Consequently, no reaction proceeded and the material was recovered.

Example 9

In a flask, 2.34 g (30 mmol) of benzene, 3.5 mg (0.02 mmol) of palladium(II) chloride, 323 mg (about 0.14 mmol) of $H_4PMo_{11}V_1O_{40}$-$nH_2O$, and 10 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that 1.27 g (8.3 mmol) of biphenyl, 0.06 g (0.3 mmol) of terphenyls, and 0.07 g (0.8 mmol) of phenol were produced.

Example 10

In a flask, 2.34 g (30 mmol) of benzene, 4.5 mg (0.02 mmol) of palladium(II) acetate, 46 mg (about 0.02 mmol) of $H_4PMo_{11}V_1O_{40}$-$nH_2O$, and 10 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that 0.83 g (5.4 mmol) of biphenyl, 0.06 g (0.2 mmol) of terphenyls, and 0.05 g (0.48 mmol) of phenol were produced. The reaction was continued for further 40 hours to find that 1.61 g (10.5 mmol) of biphenyl, 0.17 g (0.7 mmol) of terphenyls, and 0.08 g (0.8 mmol) of phenol were produced.

Example 11

A heteropolyacid was prepared by mixing 247 mg (about 0.12 mmol) of $H_3PMo_{12}O_{40}$-$nH_2O$ and 81 mg (about 0.035 mmol) of $H_4PMo_{11}V_1O_{40}$-$nH_2O$. The resulting heteropolyacid had an average vanadium content per mole of 0.25 mol, i.e., contained 0.25 gram atom of vanadium per 1 gram atom of phosphorus. In a flask, the prepared heteropolyacid, 2.34 g (30 mmol) of benzene, 4.5 mg (0.02 mmol) of palladium (II) acetate, and 10 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that 1.44 g (9.4 mmol) of biphenyl, 0.35 g (1.5 mmol) of terphenyls, and 0.07 g (0.7 mmol) of phenol were produced.

Example 12

A heteropolyacid was prepared by mixing 164 mg (about 0.07 mmol) of $H_3PMo_{12}O_{40}$-$nH_2O$ and 164 mg (about 0.07 mmol) of $H_4PMo_{11}V_1O_{40}$-$nH_2O$. The resulting heteropolyacid had an average vanadium content per mole of 0.5 mol, i.e., contained 0.5. gram atom of vanadium per 1 gram atom of phosphorus. In a flask, the prepared heteropolyacid, 2.34 g (30 mmol) of benzene, 4.5 mg (0.02 mmol) of palladium (II) acetate, and 10 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that 1.64 g (10.6 mmol) of biphenyl, 0.39 g (1.7 mmol) of terphenyls, and 0.07 g (0.7 mmol) of phenol were produced.

The above-prepared heteropolyacid was subjected to $^{31}$P-NMR analysis in heavy water (deuterium water) using phosphoric acid as an external standard. The result indicates that the prepared heteropolyacid is a mixture of two heteropolyacids other than $H_3PMo_{12}O_{40}$ and $H_4PMo_{11}V_1O_{40}$.

Example 13

A heteropolyacid was prepared by mixing 82 mg (about 0.03 mmol) of $H_3PMo_{12}O_{40}$-$nH_2O$ and 242 mg (about 0.11 mmol) of $H_4PMo_{11}V_1O_{40}$-$nH_2O$. The resulting heteropolyacid had an average vanadium content per mole of 0.75 mol, i.e., contained 0.75 gram atom of vanadium per 1 gram atom of phosphorus. In a flask, the prepared heteropolyacid, 2.34 g (30 mmol) of benzene, 4.5 mg (0.02 mmol) of palladium (II) acetate, and 10 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that 1.32 g (8.6 mmol) of biphenyl, 0.25 g (1.0 mmol) of terphenyls, and 0.05 g (0.5 mmol) of phenol were produced.

Example 14

A heteropolyacid was prepared by mixing 247 mg (about 0.11 mmol) of $H_3PMo_{12}O_{40}$-$nH_2O$ and 80 mg (about 0.03 mmol) of $H_5PMo_{10}V_2O_{40}$-$nH_2O$. The resulting heteropolyacid had an average vanadium content per mole of 0.5 mol, i.e., contained 0.5 gram atom of vanadium per 1 gram atom of phosphorus. In a flask, the prepared heteropolyacid, 2.34 g (30 mmol) of benzene, 4.5 mg (0.02 mmol) of palladium (II) acetate, and 10 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that 1.23 g (8.0 mmol) of biphenyl, 0.23 g (1.0 mmol) of terphenyls, and 0.05 g (0.5 mmol) of phenol were produced.

Example 15

A heteropolyacid was prepared by mixing 82 mg (about 0.03 mmol) of $H_3PMo_{12}O_{40}$-$nH_2O$ and 242 mg (about 0.11 mmol) of $H_5PMo_{10}V_2O_{40}$-$nH_2O$. The resulting heteropolyacid had an average vanadium content per mole of 1.5 mol, i.e., contained 1.5 gram atom of vanadium per 1 gram atom of phosphorus. In a flask, the prepared heteropolyacid, 2.34 g (30 mmol) of benzene, 4.5 mg (0.02 mmol) of palladium (II) acetate, and 10 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that 1.05 g (6.8 mmol) of biphenyl, 0.09 g (0.4 mmol) of terphenyls, and 0.02 g (0.2 mmol) of phenol were produced.

Example 16

A heteropolyacid was prepared by mixing 164 mg (about 0.07 mmol) of $H_3PMo_{12}O_{40}$-$nH_2O$ and 164 mg (about 0.07 mmol) of $H_4PMo_{11}V_1O_{40}$-$nH_2O$. The resulting heteropolyacid had an average vanadium content per mole of 0.5 mol, i.e., contained 0.5 gram atom of vanadium per 1 gram atom of phosphorus. In a flask, the prepared heteropolyacid, 4.69 g (60 mmol) of benzene, 4.5 mg (0.02 mmol) of palladium (II) acetate, and 10 ml of acetic acid were placed and were stirred at a constant temperature of 90° C. in an atmosphere of oxygen gas at 1 atm (0.1 MPa) for 27 hours. The resulting reaction mixture was analyzed by gas chromatography to find that 3.24 g (21.0 mmol) of biphenyl, 0.46 g (2.0 mmol) of terphenyls, and 0.1 g (1.1 mmol) of phenol were produced.

Example 17

In a flask, 1.17 g (15 mmol) of benzene, 1.38 g (11 mmol) of mesitylene, 4.5 mg (0.02 mmol) of palladium(II) acetate, 323 mg (about 0.14 mmol) of $H_4PMo_{11}V_1O_{40}$-$nH_2O$, and 10 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that 0.59 g (3.8 mmol) of biphenyl, 0.82 g (4.2 mmol) of 1,3,5-trimethyl-2-phenylbenzene, 0.85 g (3.6 mmol) of 1,3,5-trimethyl-2-(3', 5'-dimethylbenzyl)benzene, 0.13 g (1.4 mmol) of phenol, and 0.10 g (0.7 mmol) of 2,4,6-trimethylphenol were produced.

Example 18

In a flask, 1.17 g (15 mmol) of benzene, 2.04 g (15 mmol) of methyl benzoate, 4.5 mg (0.02 mmol) of palladium(II) acetate, 323 mg (about 0.14 mmol) of $H_4PMo_{11}V_1O_{40}$-$nH_2O$, and 10 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that 0.42 g (2.0 mmol) of methyl phenylbenzoate, 0.60 g (3.9 mmol) of biphenyl, and 0.02 g (0.2 mmol) of phenol were produced.

Example 19

In a flask, 15 mmol of benzene, 15 mmol of 2,2,4-trimethylpentane, 4.5 mg (0.02 mmol) of palladium(II) acetate, 323 mg (about 0.14 mmol) of $H_4PMo_{11}V_1O_{40}$-$nH_2O$, and 10 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that 3.8 mmol of biphenyl, 1.5 mmol of (1,1,3,3-tetramethylbutyl)benzene, and 1 mmol of phenol were produced.

Example 20

In a flask, 15 mmol of toluene, 15 mmol of mesitylene, 4.5 mg (0.02 mmol) of palladium(II) acetate, 323 mg (about 0.14 mmol) of $H_4PMo_{11}V_1O_{40}$-$nH_2O$, and 10 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that 1.7 mmol of a coupled product between toluene and toluene (a ring assembly compound with six peaks), 3.0 mmol of a coupled product between toluene and mesitylene (a ring assembly compound with three peaks), and 2.0 mmol of 1,3,5-trimethyl-2-(3', 5'-dimethylbenzyl)benzene were produced.

Example 21

In a flask, 15 mmol of p-xylene, 15 mmol of mesitylene, 4.5 mg (0.02 mmol) of palladium(II) acetate, 323 mg (about 0.14 mmol) of $H_4PMo_{11}V_1O_{40}$-$nH_2O$, and 10 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that 1.4 mmol of a coupled product between p-xylene and p-xylene(a ring assembly compound), 1.4 mmol of a coupled product between p-xylene and mesitylene (a ring assembly compound), and 1.7 mmol of 1,3,5-trimethyl-2-(3', 5'-dimethylbenzyl)benzene were produced.

Example 22

In a flask, 30 mmol of diphenyl ether, 4.5 mg (0.02 mmol) of palladium(II) acetate, 323 mg (about 0.14 mmol) of $H_4PMo_{11}V_1O_{40}$-$nH_2O$, and 10 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that 3 mmol of dibenzofuran (an intramolecularly coupled product) and 7.4 mmol of an intermolecularly coupled product of diphenyl ether were produced.

Example 23

In a flask, 30 mmol of methyl benzoate, 4.5 mg (0.02 mmol) of palladium(II) acetate, 323 mg (about 0.14 mmol) of $H_4PMo_{11}V_1O_{40}$-$nH_2O$, and 10 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that 2.4 mmol of a coupled product of methyl benzoate (a ring assembly compound) was produced.

Example 24

In a flask, 30 mmol of toluene, 4.5 mg (0.02 mmol) of palladium(II) acetate, 323 mg (about 0.14 mmol) of $H_4PMo_{11}V_1O_{40}$-$nH_2O$, and 10 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that 12.4 mmol of a coupled product of toluene (a ring assembly compound) was produced.

Example 25

In a flask, 30 mmol of anisole, 4.5 mg (0.02 mmol) of palladium(II) acetate, 323 mg (about 0.14 mmol) of $H_4PMo_{11}V_1O_{40}$-$nH_2O$, and 10 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that 7.4 mmol of a coupled product of anisole (a ring assembly compound) was produced.

Example 26

In a flask, 30 mmol of mesitylene, 4.5 mg (0.02 mmol) of palladium(II) acetate, 323 mg (about 0.14 mmol) of $H_4PMo_{11}V_1O_{40}$-$nH_2O$, and 10 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that 8.5 mmol of 1,3,5-trimethyl-2-(3', 5'-dimethylbenzyl)benzene, and 1 mmol of 2,4,6-trimethylphenol were produced.

Example 27

In a flask, 15 mmol of benzene, 2 mmol of ethyl acrylate, 0.1 mmol of palladium(II) acetate, 0.4 mmol of hydroquinone, 0.02 mmol of $H_7PMo_8V_4O_{40}$, and 5 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that ethyl cinnamate, ethyl 3,3-diphenylacrylate, and ethyl 3-acetoxyacrylate were produced in yields of 26%, 2%, and 9%, respectively.

Example 28

In a flask, 15 mmol of benzene, 2 mmol of acrylonitrile, 0.1 mmol of palladium(II) acetate, 0.4 mmol of hydroquinone, 0.02 mmol of $H_7PMo_8V_4O_{40}$, and 5 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that 3-phenylacrylonitrile was produced in a yield of 20%.

Example 29

In a flask, 15 mmol of benzene, 2 mmol of styrene, 0.1 mmol of palladium(II) acetate, 0.4 mmol of hydroquinone, 0.02 mmol of $H_7PMo_8V_4O_{40}$, and 5 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that stilbene was produced in a yield of 28%.

Example 30

In a flask, 15 mmol of benzene, 2 mmol of isobutyl acrylate, 0.1 mmol of palladium(II) acetate, 0.4 mmol of hydroquinone, 0.02 mmol of $H_7PMo_8V_4O_{40}$, and 5 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that isobutyl cinnamate was produced in a yield of 63%.

Example 31

In a flask, 15 mmol of benzene, 2 mmol of butyl acrylate, 0.1 mmol of palladium(II) acetate, 0.4 mmol of hydroquinone, 0.02 mmol of $H_7PMo_8V_4O_{40}$, and 5 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that butyl cinnamate was produced in a yield of 47%.

Example 32

In a flask, 15 mmol of benzene, 2 mmol of methyl acrylate, 0.1 mmol of palladium(II) acetate, 0.4 mmol of hydroquinone, 0.02 mmol of $H_7PMo_8V_4O_{40}$, and 5 ml of acetic acid were placed and were stirred at a constant temperature of 90° C. in an atmosphere of oxygen gas at 1 atm (0.1 MPa) for 15 hours. The resulting reaction mixture was analyzed by gas chromatography to find that methyl cinnamate was produced in a yield of 54%.

Example 33

In a flask, 15 mmol of benzene, 1.5 mmol of ethyl acrylate, 0.1 mmol of palladium(II) acetate, 0.02 mmol of $H_7PMo_8V_4O_{40}$, 0.08 mmol of sodium acetate, 0.1 mmol of acetylacetone, and 5 ml of acetic acid were placed and were stirred at a constant temperature of 90° C. in an atmosphere of oxygen gas at 1 atm (0.1 MPa) for 6 hours. The resulting reaction mixture was analyzed by gas chromatography to find that ethyl cinnamate, ethyl 3,3-diphernylacrylate, and ethyl 3-acetoxyacrylate were produced in yields of 63%, 5%, and 12%, respectively.

Example 34

In a flask, 30 mmol of benzene, 1.5 mmol of ethyl acrylate, 0.1 mmol of palladium(II) acetate, 0.02 mmol of $H_7PMo_8V_4O_{40}$, 0.08 mmol of sodium acetate, 0.1 mmol of acetylacetone, and 5 ml of propionic acid were placed and were stirred at a constant temperature of 90° C. in an atmosphere of oxygen gas at 1 atm (0.1 MPa) for 3 hours. The resulting reaction mixture was analyzed by gas chromatography to find that ethyl cinnamate and ethyl 3,3-diphenylacrylate were produced in yields of 72%, and 10%, respectively.

Example 35

The procedure of Example 34 was repeated, except that the reaction was performed for 6 hours. The resulting reaction mixture was analyzed by gas chromatography to find that ethyl cinnamate and ethyl 3,3-diphenylacrylate were produced in yields of 8%, and 73%, respectively.

Example 36

In a flask, 30 mmol of benzene, 1.5 mmol of ethyl 3-phenylacrylate, 0.1 mmol of palladium(II) acetate, 0.02 mmol of $H_7PMo_8V_4O_{40}$, 0.08 mmol of sodium acetate, 0.1 mmol of acetylacetone, and 5 ml of propionic acid were placed and were stirred at a constant temperature of 90° C. in an atmosphere of oxygen gas at 1 atm (0.1 MPa) for 3 hours. The resulting reaction mixture was analyzed by gas chromatography to find that ethyl 3,3-diphenylacrylate was produced in a yield of 84%.

Example 37

In a flask, 30 mmol of benzene, 1.5 mmol of benzalacetone, 0.1 mmol of palladium(II) acetate, 0.02 mmol of $H_7PMo_8V_4O_{40}$, 0.08 mmol of sodium acetate, 0.1 mmol of acetylacetone, and 5 ml of propionic acid were placed and were stirred at a constant temperature of 90° C. in an atmosphere of oxygen gas at 1 atm (0.1 MPa) for 3 hours. The resulting reaction mixture was analyzed by gas chromatography to find that methyl 2,2-diphenylethenyl ketone was produced in a yield of 70%.

Example 38

In a flask, 30 mmol of toluene, 1.5 mmol of ethyl acrylate, 0.1 mmol of palladium(II) acetate, 0.02 mmol of $H_7PMo_8V_4O_{40}$, 0.08 mmol of sodium acetate, 0.1 mmol of acetylacetone, and 5 ml of propionic acid were placed and were stirred at a constant temperature of 90° C. in an atmosphere of oxygen gas at 1 atm (0.1 MPa) for 2.5 hours. The resulting reaction mixture was analyzed by gas chromatography to find that ethyl 3-[(o, m, or p)-methylphenyl]acrylate was produced in a yield of 70% (o-isomer:m-isomer:p-isomer=15:42:43).

Example 39

In a flask, 30 mmol of chlorobenzene, 1.5 mmol of ethyl acrylate, 0.1 mmol of palladium(II) acetate, 0.02 mmol of $H_7PMo_8V_4O_{40}$, 0.08 mmol of sodium acetate, 0.1 mmol of acetylacetone, and 5 ml of propionic acid were placed and were stirred at a constant temperature of 90° C. in an atmosphere of oxygen gas at 1 atm (0.1 MPa) for 6 hours. The resulting reaction mixture was analyzed by gas chromatography to find that ethyl 3-[(o, m, or p)-chlorophenyl]acrylate was produced in a yield of 68% (o-isomer:m-isomer:p-isomer=27:40:44).

Example 40

In a flask, 30 mmol of bromobenzene, 1.5 mmol of ethyl acrylate, 0.1 mmol of palladium(II) acetate, 0.02 mmol of $H_7PMo_8V_4O_{40}$, 0.08 mmol of sodium acetate, 0.1 mmol of acetylacetone, and 5 ml of propionic acid were placed and were stirred at a constant temperature of 90° C. in an atmosphere of oxygen gas at 1 atm (0.1 MPa) for 7 hours. The resulting reaction mixture was analyzed by gas chromatography to find that ethyl 3-[(o, m, or p)-bromophenyl]acrylate (o-isomer:m-isomer:p-isomer=38:35:27) and ethyl cinnamate were produced in yields of 49% and 4%, respectively.

Example 41

In a flask, 5 mmol of naphthalene, 1.5 mmol of ethyl acrylate, 0.1 mmol of palladium(II) acetate, 0.02 mmol of $H_7PMo_8V_4O_{40}$, 0.08 mmol of sodium acetate, 0.1 mmol of acetylacetone, and 5 ml of propionic acid were placed and were stirred at a constant temperature of 90° C. in an atmosphere of oxygen gas at 1 atm (0.1 MPa) for 4 hours. The resulting reaction mixture was analyzed by gas chromatography to find that ethyl 3-naphthylacrylate was produced in a yield of 42% ($\alpha$-isomer:$\beta$-isomer=66:34).

Example 42

In a flask, 3 mmol of furan, 1.5 mmol of ethyl acrylate, 0.1 mmol of palladium(II) acetate, 0.02 mmol of $H_7PMo_8V_4O_{40}$, 0.08 mmol of sodium acetate, 0.1 mmol of acetylacetone, and 5 ml of propionic acid were placed and were stirred at a constant temperature of 50° C. in an atmosphere of oxygen gas at 1 atm (0.1 MPa) for 3 hours. The resulting reaction mixture was analyzed by gas chromatography to find that ethyl 3-(2-furyl)acrylate and 2,5-bis(2-ethoxycarbonylethenyl)furan were produced in yields of 51%0 and 18%, respectively.

Example 43

In a flask, 45 mmol of benzene, 3 mmol of ethyl acrylate, 0.03 mmol of palladium(II) acetate, 0.02 mmol of $H_3PMo_{12}O_{40}$, 0.08 mmol of sodium acetate, 0.03 mmol of acetylacetone, and 5 ml of propionic acid were placed and were stirred at a constant temperature of 90° C. in an atmosphere of oxygen gas at 1 atm (0.1 MPa) for 12 hours. The resulting reaction mixture was analyzed by gas chromatography to find that ethyl cinnamate and ethyl 3,3-diphenylacrylate were produced in yields of 19% and 1%, respectively.

Example 44

In a flask, 45 mmol of benzene, 3 mmol of ethyl acrylate, 0.03 mmol of palladium(II) acetate, 0.02 mmol of $H_4PMo_{11}V_1O_{40}$, 0.08 mmol of sodium acetate, 0.03 mmol of acetylacetone, and 5 ml of propionic acid were placed and were stirred at a constant temperature of 90° C. in an atmosphere of oxygen gas at 1 atm (0.1 MPa) for 12 hours.

The resulting reaction mixture was analyzed by gas chromatography to find that ethyl cinnamate and ethyl 3,3-diphenylacrylate were produced in yields of 66% and 10%, respectively.

Example 45

In a flask, 45 mmol of benzene, 3 mmol of ethyl acrylate, 0.03 mmol of palladium(II) acetate, 0.01 mmol of $H_3PMo_{12}O_{40}$, 0.1 mmol of $H_4PMo_{11}V_1O_{40}$, 0.08 mmol of sodium acetate, 0.03 mmol of acetylacetone, and 5 ml of propionic acid were placed and were stirred at a constant temperature of 90° C. in an atmosphere of oxygen gas at 1 atm (0.1 MPa) for 12 hours. The resulting reaction mixture was analyzed by gas chromatography to find that ethyl cinnamate and ethyl 3,3-diphenylacrylate were produced in yields of 73% and 8%, respectively.

Example 46

The procedure of Example 45 was repeated, except that the reaction was performed for 24 hours. The resulting reaction mixture was analyzed by gas chromatography to find that ethyl cinnamate and ethyl 3,3-diphenylacrylate were produced in yields of 27% and 54%, respectively.

Example 47

In a flask, 5 mmol of thiophene, 1.5 mmol of ethyl acrylate, 0.1 mmol of palladium(II) acetate, 0.02 mmol of $H_7PMo_8V_4O_{40}$, 0.08 mmol of sodium acetate, 0.1 mmol of acetylacetone, and 5 ml of propionic acid were placed and were stirred at a constant temperature of 90° C. in an atmosphere of oxygen gas at 1 atm (0.1 MPa) for 6 hours. The resulting reaction mixture was analyzed by gas chromatography to find that ethyl 3-(2-thienyl)acrylate was produced in yield of 60%.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A process for producing an aromatic compound, comprising the step of:
   bringing an aromatic compound (B) into contact with molecular oxygen (C) in the presence of a catalyst (A) and further in the presence of the a reducing agent (D) to thereby yield a corresponding aromatic compound (G1),
   the catalyst (A) comprising at least one of (A1) a heteropolyacid and/or a salt thereof, and (A2) a mixture of oxoacids and/or salts thereof containing, as a whole, one of P and Si and at least one selected from the group consisting of V, Mo, and W.

2. The process according to claim 1, wherein the heteropolyacid and/or a salt thereof (A1) comprises, as its constitutional elements, one of P and Si and at least one selected from the group consisting of V, Mo, and W.

3. The process according to one of claims 1 and 2, wherein the heteropolyacid and/or a salt thereof (A1) is at least one of phosphovanadomolybdic acids, phosphomolybdic acids, and salts thereof represented by the following formula:

$$A_{3+n}[PMo_{12-n}V_nO_{40}]$$

wherein A is at least one selected from the group consisting of hydrogen atom, $NH_4$, alkali metals, and alkaline earth metals; and n is an integer from 0 to 10.

4. The process according to claim 1, wherein the catalyst (A) comprises one of P and Si, 10.5 to 11.9 gram atom of Mo, and 0.1 to 1.5 gram atom of V relative to 1 gram atom of the one of P and Si.

5. The process according to claim 1, wherein the reducing agent (D) is at least one selected from the group consisting of carbon monoxide, hydrogen, silanes, aldehydes and alcohols.

* * * * *